(12) United States Patent
Pastor et al.

(10) Patent No.: US 6,579,328 B2
(45) Date of Patent: Jun. 17, 2003

(54) TRANSITION-METAL-CATALYZED PROCESS FOR THE PREPARATION OF STERICALLY HINDERED N-SUBSTITUTED ARYLOXYAMINES

(75) Inventors: Stephen D. Pastor, Danbury, CT (US); Sai Ping Shum, Jamesburg, NJ (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 107 days.

(21) Appl. No.: 09/824,149

(22) Filed: Apr. 2, 2001

(65) Prior Publication Data

US 2002/0007585 A1 Jan. 24, 2002

Related U.S. Application Data

(60) Provisional application No. 60/200,988, filed on May 1, 2000, now abandoned.

(51) Int. Cl.$^7$ ............... C11C 5/00; C10L 5/00
(52) U.S. Cl. ............ 44/275; 544/163; 544/180; 544/186; 544/224; 548/100; 548/146; 548/215; 548/240; 548/400; 548/517; 548/525; 549/456; 564/300
(58) Field of Search ............ 44/275; 544/163, 544/224, 186, 180; 548/100, 146, 215, 240, 400, 517, 525; 549/456; 564/300

(56) References Cited

U.S. PATENT DOCUMENTS

| | | | | |
|---|---|---|---|---|
| 3,530,084 | A | 9/1970 | Potts | 260/28.5 |
| 4,379,721 | A | 4/1983 | Qualitz et al. | 106/21 |
| 4,416,966 | A | 11/1983 | Sanders et al. | 430/138 |
| 4,483,912 | A | 11/1984 | Sanders | 430/138 |
| 4,535,050 | A | 8/1985 | Adair et al. | 430/138 |
| 4,535,463 | A | 8/1985 | Ito et al. | 377/8 |
| 4,551,407 | A | 11/1985 | Sanders et al. | 430/138 |
| 4,562,137 | A | 12/1985 | Sanders | 430/138 |
| 4,608,330 | A | 8/1986 | Marabella | 430/138 |
| 4,616,051 | A | 10/1986 | Paolino | 524/102 |
| 5,089,477 | A | 2/1992 | Fregly et al. | 514/23 |
| 5,364,749 | A | 11/1994 | Leppard et al. | 430/507 |
| 5,964,905 | A | 10/1999 | Camp et al. | 44/275 |

FOREIGN PATENT DOCUMENTS

| | | |
|---|---|---|
| EP | 0139479 | 9/1987 |
| EP | 0237024 | 9/1987 |
| EP | 0162664 | 9/1989 |
| EP | 0164931 | 10/1990 |
| EP | 0507734 | 10/1992 |
| EP | 0237025 | 10/1993 |
| EP | 0260129 | 5/1994 |
| JP | 3278554 | 12/1991 |
| WO | 00/22037 | 4/2000 |

OTHER PUBLICATIONS

Chemical Abstract of Braslau,Povazancova, Moad and Scott (all cited on Applicant's 1449); 1997; 1990; 1980, respectively.*
Abstract for JP 3278554 (1991).
M. Doyle et al., J. Org. Chem., vol. 42, No. 14, (1977), pp. 2426–2431.
R. Braslau et al., Macromolecules, (1997), vol. 30, pp. 6445–6450.
G. Moad et al., Aust. J. Chem., (1983), vol. 36, pp. 1573–1588.
A. Scott et al., J.C.S. Perkin II, (1980) pp. 26–266.
D. Witt et al.,Heteroatom Chemistry, vol. 10, No. 5 (1999) pp. 431–439.
M. Povazancova et al., Die Angewandte Makromolekulare Chemie, 176/177 (1990) pp. 291–301.
L. J. Beckwith et al., J. Chem. Soc., Chem. Commun., (1981), pp. 595–597.
H Zollinger et al., Helv. Chimica Acta, vol. 59, p. 1438, (1976).
Abstact for EP 0507734 (1992).

\* cited by examiner

*Primary Examiner*—Cephia D. Toomer
(74) *Attorney, Agent, or Firm*—Tyler A. Stevenson; Luther A. R. Hall

(57) ABSTRACT

Sterically hindered N-substituted aryloxyamines are prepared by the transition-metal-catalyzed decomposition of diazonium salts in the presence of a sterically hindered nitroxyl radical. These compounds are useful as thermal and light stabilizers for a variety of organic substrates.

24 Claims, No Drawings

TRANSITION-METAL-CATALYZED PROCESS FOR THE PREPARATION OF STERICALLY HINDERED N-SUBSTITUTED ARYLOXYAMINES

This application claims benefit under 35 USC 119(e) of U.S. provisional application Ser. No. 60/200,988, filed on May 1, 2000 now abandoned.

This invention pertains to the novel process for preparing sterically hindered N-substituted aryloxyamines by the transition-metal-catalyzed decomposition of a diazonium salt in the presence of a sterically hindered nitroxyl radical.

BACKGROUND OF THE INVENTION

N-Aryloxyamines have been prepared in the prior art by the reaction of a phenylhydrazine with a stable nitroxide. In certain instances, N-aryloxyamines have been prepared in low yield by the decomposition of aryldiazonium salts in the presence of a nitroxyl radical, but without a transition metal catalyst being present. These papers are often about mechanistic studies with poor yields and state that the reaction described is limited in scope. A. C. Scott et al., J. Chem. Soc., Perkin Trans. 2, 1980, 260–266.

In another study, an aryl radical formed from a diazonium salt added intramolecularly to a double bond and the result alkyl radical was trapped by a stable nitroxyl radical. L. J. Beckwith and G. F. Meijs, J. Chem. Soc., Chem. Commun. 1981, 595–597.

In respect to wax stabilization, the use of selected hindered amines and/or benzotriazole UV absorbers is known in the prior art. This is seen in Japanese Hei 3-278554; WO 00/22037; and U.S. Pat. Nos. 3,530,084; 4,379,721; 4,616,051 and 5,964,905 and copending applications Ser. Nos. 09/495,495, 09/495,496 and 09/741,583.

It is clear that the instant process is a facile and direct way to prepare these interesting and useful stabilizer compounds in yields far exceeding anything found in the prior art.

DETAILED DISCLOSURE

The instant invention pertains to a process for preparing a sterically hindered N-aryloxyamine of formula I, II, III, IV, V or VI

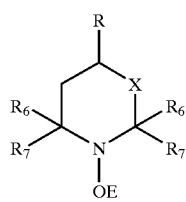
(I)

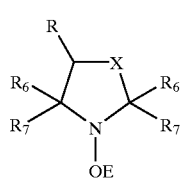
(II)

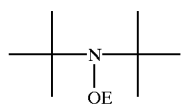
(III)

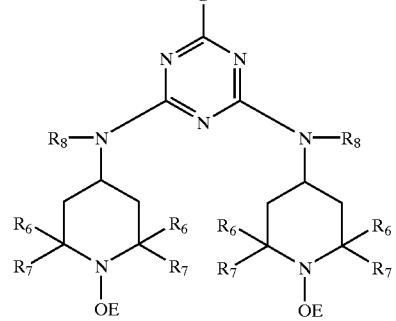
(IV)

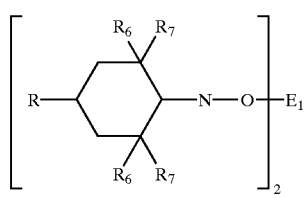
(V)

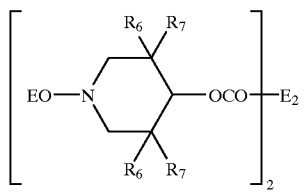
(VI)

which comprises reacting a sterically hindered nitroxyl compound of formula VII, VIII, IX, X or XI

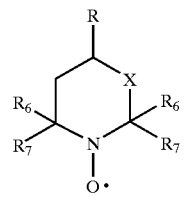
(VII)

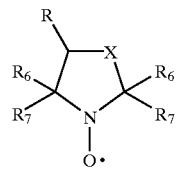
(VIII)

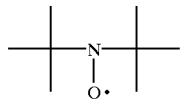
(IX)

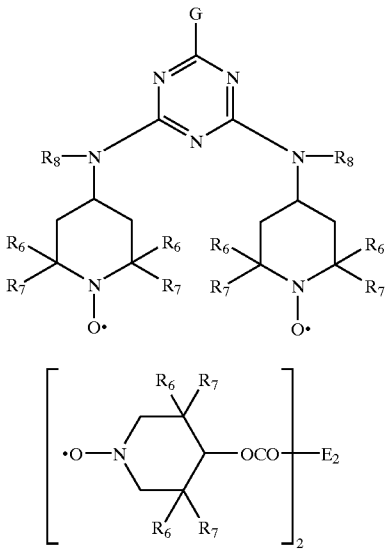

with a diazonium salt of an aromatic amine of formula XII, XIII or XIV

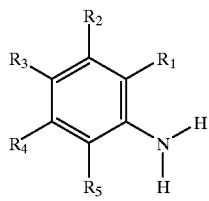

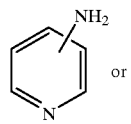

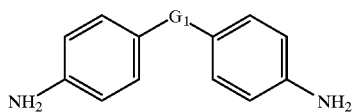

in the presence of a transition-metal catalyst wherein

X is —CH$_2$—, —O—, —S— or —NR$_8$— where R$_8$ is hydrogen or alkyl of 1 to 12 carbon atoms, R$_6$ and R$_7$ are independently alkyl of 1 to 8 carbon atoms, or R$_6$ and R$_7$ together are tetramethylene or pentamethylene,

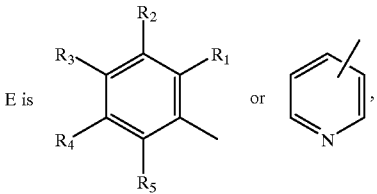

E$_1$ is

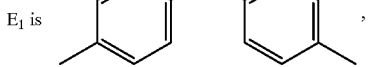

E$_2$ is alkylene of 2 to 12 carbon atoms,

G is chloro or —N(2-ethylhexyl)$_2$,

G$_1$ is —CH$_2$—, —CO— or —O—,

R is hydrogen, alkyl of 1 to 18 carbon atoms, aralkyl of 7 to 15 carbon atoms, aryl of 6 to 10 carbon atoms, hydroxyl, carboxyl, amino, alkylamino of 1 to 18 carbon atoms, dialkylamino of 2 to 36 carbon atoms, oxo, alkylthio of 1 to 18 carbon atoms, alkoxy of 1 to 18 carbon atoms, aryloxy of 7 to 15 carbon atoms, benzoyloxy, alkylcarbonyloxy of 2 to 18 carbon atoms or alkylcarbonylamino of 2 to 18 carbon atoms, and R$_1$ to R$_5$ are independently hydrogen, halogen, nitro, cyano, alkyl of 1 to 18 carbon atoms, aralkyl of 7 to 15 carbon atoms, aryl of 6 to 10 carbon atoms, hydroxyl, carboxyl, alkylthio of 1 to 18 carbon atoms, alkoxy of 1 to 18 carbon atoms, aryloxy of 7 to 15 carbon atoms, alkylcarbonyloxy of 1 to 18 carbon atoms, alkylsulfonyl of 1 to 18 carbon atoms, arylsulfonyl of 6 to 15 carbon atoms, sulfo or —P(O)(OH)$_2$ or —P(O)(OR$_6$)$_2$, or any two vicinal substituents connected together to form a mono or polycyclic ring, so that formula XII can represent inter alia 1-naphthylamine or 2-naphthylamine; or any two vicinal carboxyl groups can be joined to form an imide; or R$_3$ is 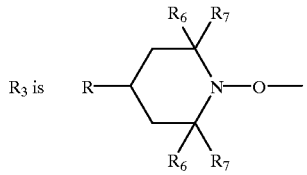

where R, R$_6$ and R$_7$ are as defined above.

The diazonium salt of the aromatic amine of formula XII can be prepared by reaction with an alkyl nitrite ester, such as tert-butyl nitrite. The diazonium salt can also be prepared using a nitrite salt and an acid, such as sodium nitrite and hydrochloric acid.

Indeed, the instant compounds can be made directly from nitroxides which are commercially available such as TEMPO (1-oxyl-2,2,6,6-tetramethylpiperidine), 4-OXOTEMPO (1-oxyl-2,2,6,6-tetramethyl-4-oxopiperidine) and di-tert-butyl nitroxide.

The reaction is conveniently carried out in acetonitrile as solvent at a temperature of 0 to 100° C., or between 20 and 70° C.

The transition metal is a metal of Group 4, 5, 6, 7, 8, 9 or 10 of the periodic table; for example copper(I), copper(II), cobalt(II), manganese(II), titanium(III), gold(I), iron(II), iron(III), cobalt(II), nickel(II) or chromium(III).

The process is carried out in the presence of 0.1 mole % to stoichiometric quantities of the transition metal catalyst.

In another embodiment, the transition metal catalyst is copper(I) or copper (II), for example copper(II) fluoride.

In still another embodiment, the transition metal catalyst is gold(I) chloride.

In still other embodiments of the invention, the transition metal catalyst is (S,S)-(+)-N,N-bis(3,5-di-tert-butylsalicylidene)-1,2-cyclohexanediaminocobalt(II), N,N-bis(salicylidene)ethylenediaminocobalt(II) or (R,R)-(−)-N,N-bis(3,5-di-tert-butylsalicylidene)-1,2-cyclohexanediaminocobalt(II).

In another embodiment, X is methylene.

In other embodiments, R is hydrogen, hydroxyl, oxo or acetamido.

For example, $R_1$ to $R_5$ are each hydrogen; or $R_1$ is nitro, $R_3$ is chloro or trifluoromethyl, and $R_2$, $R_4$ and $R_5$ are hydrogen; or $R_1$ and $R_3$ are bromo, and $R_2$, $R_4$ and $R_5$ are hydrogen.

In another embodiment, $R_6$ and $R_7$ are each methyl.

In another embodiment, $R_1$ and $R_3$ are each bromo or chloro.

A further aspect of this invention is the addition of pyridine to the reaction mixture either as a component of the reaction mixture or as the solvent in the presence of the transition metal catalyst. Pyridine has been found to increase further the yield of the reaction as well as having superior solvent properties in certain cases. For example, when the diazonium salt is made using sodium nitrite and hydrochloric acid, pyridine also serves as a basic medium for neutralizing excess acid.

The stabilization of diazonium salts by pyridine has been reported by Heinrich Zollinger et al. (Helv. Chimica Acta, 59, 1438 (1976). Furthermore it is stated that pyridine promotes a homolytic radical pathway. Without a transition metal catalyst, however, the homolytic cleavage at 70° C. is slow and is not useful.

The instant invention also pertains to a composition stabilized which comprises (a) an organic material subject to degradation by heat, light or oxygen, and (b) an effective stabilizing amount of a compound of formula I, II or III as described above.

For example, the organic material is a natural, semi-synthetic or synthetic polymer, especially a thermoplastic polymer.

In another embodiment, the polymer is a polyolefin or polycarbonate; for example, polyethylene or polypropylene; or is polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalenedicarboxylate), or other blends or copolymers such as poly(ethylene/1,4-cyclohexylenedimethylene terephthalate) PETG or an ionomer as described on page 29.

In another embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

For example, the resin is a thermoset acrylic melamine resin or an acrylic urethane resin.

In yet another embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula I, II or III can be incorporated into the carder material as early as the production of the latter, in the production of paper, for example, being added to the paper pulp. A second method of application is to spray the carder material with an aqueous solution of compounds of formula I, II or III or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, high-speed stirrers and the like. The compounds of formula I, II or III can be easily incorporated into the coating composition.

The recording material according to this invention contains 1 to 5000 $mg/m^2$; or 50–1200 $mg/m^2$, of a compound of formula I, II or III.

As already mentioned, the recording materials according to the invention embrace a wide field. The compounds of formula I, II or III can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula I, II or III act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula I, II or III can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and pen-plotters. Of the above, recording materials for dye diffusion transfer printing are useful, for example, as described in EP-A 507,734.

The instant compounds can also be employed in inks, preferably for ink jet printing, for example, as described in U.S. Pat. No. 5,098,477 which is incorporated herein by reference.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

Some compounds are those in which one of X and Y is —O—; and those in which both X and Y are —O—.

In general polymers which can be stabilized include
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

31. Polysiloxanes such as the soft, hydrophilic polysiloxanes described, for example, in U.S. Pat. No. 4,259,467; and the hard polyorganosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%. However, some high performance films or in UV absorbing layers of laminates such as those produced by coextrusion may contain from 5–15% by weight of the instant compounds. Concentrations of 5–10% by weight are typical in certain coextrusion applications.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.
1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
1.7. Esters of β-(3,5-di-tert-butyl-4-hydroxyphenyl)-propionic acid with monohydric or polyhydric alcohols, for example,
methanol
diethylene glycol
octadecanol
triethylene glycol
1,6-hexanediol
pentaerythritol
neopentyl glycol
tris-hydroxyethyl isocyanurate
thiodiethylene glycol
di-hydroxyethyl oxalic acid diamide
triethanolamine
triisopropanolamine
1.8. Esters of β-(5-tert-butyl-4-hydroxy-3-methylphenyl)-propionic acid with monohydric or polyhydric alcohols, for example,
methanol
diethylene glycol
octadecanol
triethylene glycol
1,6-hexanediol
pentaerythritol
neopentyl glycol
tris-hydroxyethyl isocyanurate
thiodiethylene glycol
di-hydroxyethyl oxalic acid diamide
triethanolamine
triisopropanolamine
1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis (1-octyloxy-2,2,6,6-tetramethylpiperidin-4-yl) sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenyllylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzyl-hydroxylamine, N,N-diethylhydroxylamine, N,N-dioctylhydroxylamine, N,N-dilaurylhydroxylamine, N,N-ditetradecylhydroxylamine, N,N-dihexadecylhydroxyl-amine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Amine Oxides, for example, tridecyl amine oxide, tri-dodecyl amine oxide, trihexadecyl amine oxide, tri($C_{12}$–$C_{14}$ alkyl) amine oxide, tri($C_{16}$–$C_{18}$ alkyl) amine oxide, tri ($C_{20}$–$C_{22}$ alkyl) amine oxide, di($C_{12}$–$C_{14}$ alkyl) methyl amine oxide, di($C_{16}$–$C_{18}$ alkyl) methyl amine oxide, di($C_{20}$–$C_{22}$ alkyl) methyl amine oxide, di(tallow alkyl) methyl amine oxide, di(coco alkyl) methyl amine oxide.

9. Polyamide stabilizers, for example copper salts in combination with iodides and/or phosphorus compounds and salts of divalent manganese.

10. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

11. Nucleating agents, for example, 4-tert-butyl-benzoic acid, adipic acid, diphenylacetic acid.

12. Fillers and reinforcing agents, for example, calcium carbonate, silicates, glass fibers, asbestos, talc, kaolin, mica, barium sulfate, metal oxides and hydroxides, carbon black, graphite.

13. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

14. Benzofuranones and indolinones, for example those disclosed in U.S. Pat. No. 4,325,863, U.S. Pat. No. 4,338,244 or U.S. Pat. No. 5,175,312, or 3-[4-(2-acetoxyethoxy) phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-di-methylphenyl)-5,7-di-tert-butyl-benzofuran-2-one, 3-(3,5-dimethyl-4-pivaloyloxyphenyl)-5,7-di-tert-butyl-benzofuran-2-one.

The co-stabilizers, with the exception of the benzofuranones listed under 14, are added for example in concentrations of 0.01 to 10%, relative to the total weight of the material to be stabilized.

Further compositions comprise, in addition to components (a) and (b) further additives, such as phenolic antioxidants, light stabilizers or processing stabilizers.

These additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also the benzofuran-2-ones, such as described, for example, in U.S. Pat. No. 4,325,863, U.S. Pat. No. 4,338,244 or U.S. Pat. No. 5,175,312.

For examples, the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3,-tris(2-methyl-4-hydroxy-5-tert-butylphenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

Another embodiment is the phenolic antioxidant which is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yl-n-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

Another hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2, 2,6,6-tetramethylpiperidin-4-yl) succinate, 1-octyloxy-2,2, 6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The instant composition can additionally contain another UV absorber selected from the group consisting of the benzotriazoles, s-triazines, the oxanilides, the hydroxybenzophenones, benzoates and the α-cyanoacrylates.

The instant composition may additionally contain an effective stabilizing amount of at least one other 2-hydroxyphenyl-2H-benzotriazole; another tris-aryl-s-triazine; or hindered amine or mixtures thereof.

The 2-hydroxyphenyl-2H-benzotriazole is selected from the group consisting of
2-(2-hydroxy-3,5-di-tert-amylphenyl)-2H-benzotriazole;
2-[2-hydroxy-3,5-di(α,α-dimethylbenzyl)phenyl]-2H-benzotriazole;
2-[2-hydroxy-3-(α,α-dimethylbenzyl)-5-tert-octylphenyl]-2H-benzotriazole;
2-{2-hydroxy-3-tert-butyl-5-[2-(omega-hydroxy-octa (ethyleneoxy)carbonyl)ethyl]phenyl}-2H-benzotriazole;
5-chloro-2-(2-hydroxy-3,5-di-tert-butylphenyl)-2H-benzotriazole;
5-chloro-2-(2-hydroxy-3-tert-butyl-5-methylphenyl)-2H-benzotriazole;
2-(2-hydroxy-5-tert-octylphenyl)-2H-benzotriazole; and
2-{2-hydroxy-3-tert-butyl-5-[2-(octyloxy)carbonyl)ethyl]phenyl}-2H-benzotriazole.

The other tris-aryl-s-triazine is selected from the group consisting of
2,4-bis(2,4-dimethylphenyl)-6-(2-hydroxy-4-octyloxyphenyl)-s-triazine;
2,4-diphenyl-6-(2-hydroxy-4-hexyloxyphenyl)-s-triazine;
2,4-bis(2,4-dimethylphenyl)-6-[2-hydroxy-4-(3-do-/tridecyloxy-2-hydroxypropoxy)phenyl]-s-triazine; and
2-(2-hydroxyethylamino)-4,6-bis[N-butyl-N-(1-cyclohexyloxy-2,2,6,6-tetramethylpiperidin-4-yl)amino]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, such as in the case of retouching finishes, as well as various coil coating applications. The lacquers stabilized in accordance with the invention are applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like.

Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be especially useful in other applications where their enhanced durability is required such as in solar films and the like.

Some of the instant compounds of formulas I, II, III, IV, V or VI are novel. These include
(i) 1-(2-nitro-4-trifluoromethylphenoxy)-2,2,6,6-tetramethylpiperidine;
(ii) 1-(2-nitro-4-chlorophenoxy)-2,2,6,6-tetramethylpiperidine;
(iii) 1-(2,4-dibromophenoxy)-2,2,6,6-tetramethylpiperidine;
(iv) 1-(2,4-dibromophenoxy)-4-hydroxy-2,2,6,6-tetramethylpiperidine;
(v) 1-(2,4-dibromophenoxy)-4-acetamido-2,2,6,6-tetramethylpiperidine;
(vi) 1-(2,4-dibromophenoxy)-4-oxo-2,2,6,6-tetramethylpiperidine;
(vii) 1-(2-naphthyloxy)-2,2,6,6-tetramethylpiperidine;
(viii) 1-(4-benzoylphenoxy)-2,2,6,6-tetramethylpiperidine;
(ix) 1-phenoxy-4-benzoyloxy-2,2,6,6-tetramethylpiperidine;
(x) N-phenoxy-di-tert-butylamine;
(xi) 2,4-bis[N-butyl-N-(1-phenoxy-2,2,6,6-tetramethylpiperidin-4-yl)amino]-6-chloro-s-triazine;
(xii) 2,4-bis{N-butyl-N-[1-(2,4-dibromophenoxy)-2,2,6,6-tetramethylpiperidin-4-yl]amino}-6-[N,N-bis(2-ethylhexyl)amino]-s-triazine;
(xiii) 2,4-bis[N-butyl-N-(1-phenoxy-2,2,6,6-tetramethylpiperidin-4-yl)amino]-6-[N,N-bis(2-ethylhexyl)amino]-s-triazine;
(xiv) 1-(3,5-di-tert-butylphenoxy)-2,2,6,6-tetramethylpiperidine;
(xv) 1-(pyridin-3-yloxy)-2,2,6,6-tetramethylpiperidine;
(xvi) 1-(2-nitro-4-chlorophenoxy)-2,2,6,6-tetramethyl-4-hydroxypiperidine;
(xvii) 4,4'-bis(2,2,6,6-tetramethylpiperidin-1-yloxy)benzophenone;
(xviii) di(1-phenoxy-2,2,6,6-tetramethyl-piperidin-4-yl)sebacate;
(xix) 5-[4-(2,2,6,6-tetramethylpiperidin-1-yloxy)-phenyl]-2-(2-hydroxy-3-α-cumyl-5-tert-octylphenyl)-2H-benzotriazole;
(xx) 4,4'-bis[(4-hydroxy-2,2,6,6-tetramethylpiperidin-1-yl)oxy]diphenylmethane, or
(xxi) 1-(phthalimid-4-yloxy)-4-hydroxy-2,2,6,6-tetramethylpiperidine.

Still another embodiment of the instant invention is a composition which comprises
(a) candle wax which is white and scented, white and unscented, dyed and scented, dyed and unscented, dipped and scented or dipped and unscented, and
(b) an effective stabilizing amount of a compound of formula I, II or III as described above.

It should be noted that candles contain a host of various components. The base materials may be made up of the following:
paraffin wax,
natural oils,
polyamide plus fatty acid/ester,
fatty acids such as stearin,
opacifiers,
beeswax,
glycerides plus oxidized wax,
alcohols, and
ethylene oligomers.

Candles also contain a number of additives such as the following:
mold release agents,
fragrances,
insect repellants or insecticides,
hardeners,
crystal modifiers,
clarifiers,
guttering reducers,
colorants,
f.p. control agents,
stretchability improvers,
gelling agents,
extrusion aids, and
vortex reducers.

Each of the various components are meant to control or modify the properties of the candle to insure proper burning, reduce channelling, aid in uniform melting, and the like. The colorants and fragrances obviously are there to provide the proper color, scent or other aesthetic appeal.

Of increasing importance are the transparent gel candles which look like clear glass, but which burn like a classical candle. As is discussed in detail in U.S. Pat. No. 5,879,694, the relevant parts of which are incorporated herein by reference, these gel candles usually contain a copolymer selected from the group consisting of a triblock, radial block, diblock or multiblock copolymer classically made up of at least two thermodynamically incompatible segments containing both hard and soft segments. Typical of such block copolymers is KRATON® (Shell Chemical Co.) which consists of block segments of styrene monomer units and rubber monomer or comonomer units. The most common structure found in KRATON® D series is a linear ABA block with styrene-butadiene-styrene (SBS) or styrene-isoprene-styrene (SIS).

The following examples are for illustrative purposes only and are not to be construed to limit the scope of the invention in any manner whatsoever.

EXAMPLE 1

1-Phenoxy-2,2,6,6-tetramethylpiperidine

This example shows the use of 0.3 mol % of copper(II) fluoride based on aniline and with 3 molar excess of aniline.

To a suspension of 3.9 g (25 mmol) of 1-oxyl-2,2,6,6-tetramethylpiperidine, 11.76 g (114 mmol) of tert-butyl nitrite and 25 mg (0.25 mmol) of copper(II) fluoride in 120 mL of acetonitrile at 65° C. under a nitrogen atmosphere is added dropwise over 30 minutes 6.98 g (75 mmol) of aniline. The evolution of gas is observed during the addition of the aniline. The dark red reaction mixture is kept at 65° C. for an additional ten minutes followed by cooling to ambient temperature. The reaction mixture is then concentrated to a thick oil which turns into a semi-solid upon standing. The residue is purified by vacuum flash chromatography (heptane) to give 4.3 g of a colorless oil in 74.1% yield based on nitroxyl. The structure is confirmed by $^1$Hnmr analysis, mass spectroscopy and elemental analyses.

$^1$Hnmr ($C_6D_6$) (300.08 MHz) d 1.42, 1.20, 1.12 (overlapping m, $CH_2$, 6H), 1.16 (s, $CH_3$, 6H), 1.017 (s, $CH_3$, 6H), 7.25 (d, 2H, $^3J_{HH'}$=8.2 Hz), 7.12 (dd, CH, 2H, $^3J_{HH'}$=8.3 Hz), $^3J_{HH''}$=8.2 Hz), 6.78 (tt, CH, 1H, $^3J_{HH'}$=7.2 Hz, $^4J_{HH''}$=1.2 Hz); MS m/s 233. Analysis: Calcd for $C_{15}H_{23}NO$: C, 77.2; H, 9.9; N, 6.0. Found: C, 77.1; H, 9.9; N, 6.0.

EXAMPLE 2

1-Phenoxy-2,2,6,6-tetramethyl-4-hydroxypiperidine

The procedure of Example 1 is repeated using 17.2 g (100 mmol) of 1-oxyl-2,2,6,6-tetramethyl-4-hydroxypiperidine, 3.92 g (38 mmol) of tert-butyl nitrite, 3 g (30 mmol) of copper(II) fluoride, 120 mL of acetonitrile and 2.32 g (25 mmol) of aniline at 65° C. The crude product obtained is purified by vacuum flash chromatography (25% ethyl acetate/heptane) to give 3.3 g of a solid melting at 144–146° C., a 53% yield based on the aniline. The structure is confirmed by $^1$Hnmr and mass spectroscopy analyses.

$^1$Hnmr ($CDCl_3$) (300.08 MHz) d 1.94, 1.76, 1.62 (overlapping m, $CH_2$, 4H), 1.30 (s, $CH_3$, 6H), 1.07 (s, $CH_3$, 6H), 4.05 (m, CH, 1H), 7.22 (overlapping m, CH, 4H), 6.87 (tt, CH, 1H $^3J_{HH'}$=6.8 Hz, $^4J_{HH''}$=1.6 Hz); MS m/s 249. Analysis: Calcd for $C_{15}H_{23}NO_2$: C, 72.3; H, 9.3; N, 5.6. Found: C, 72.2; H, 9.3; N, 5.4.

EXAMPLE 3

1-Phenoxy-2,2,6,6-tetramethylpiperidine

This example shows the effect of excess nitroxyl and a greater than stoichiometric amount of copper(II) fluoride catalyst.

Into a suspension of 15.6 g (100 mmol) of 1-oxyl-2,2,6, 6-tetramethylpiperidine, 3.92 g (38 mmol) of tert-butyl nitrite and 3 g (30 mmol) of copper(II) fluoride in 120 mL of acetonitrile at 65° C. is added dropwise 2.32 g (25 mmol) of aniline. During the addition, the evolution of gas is observed. After 30 minutes of addition time, the dark red reaction mixture is kept at 65° C. for an additional ten minutes followed by cooling to ambient temperature. The reaction mixture is then concentrated to a thick oil which turns into a semi crude solid on standing. The crude product is purified by vacuum flash chromatography (heptane) to give 2.3 g of a colorless oil in 39.6% yield based on the starting aniline. The structure of the product is confirmed by $^1$Hnmr and mass spectroscopy analyses.

$^1$Hnmr ($C_6D_6$) (300.08 MHz) d 1.42, 1.29, 1.12 (overlapping m, $CH_2$, 6H), 1.16 (s, $CH_3$, 6H), 1.017 (s, $CH_3$, 6H), 7.25 (d, 2H, $^3J_{HH'}$=8.2 Hz), 7.12 (dd, CH, 2H, $^3J_{HH'}$=8.3 Hz), $^3J_{HH''}$=8.2 Hz), 6.78 (tt, CH, 1H, $^3J_{HH'}$=7.2 Hz, $^4J_{HH''}$=1.2 Hz); MS m/s 233.

EXAMPLE 4

1-Phenoxy-2,2,6,6-tetramethylpiperidine

This example shows the effect of excess nitroxyl and 5.2 mol % copper(II) catalyst The procedure of Example 1 is repeated using 15.6 g (100 mmol) of 1-oxyl-2,2,6,6-tetramethylpiperidine, 3.92 g (38 mmol) of tert-butyl nitrite, 0.13 g (1.3 mmol (of copper(II) fluoride, 120 mL of acetonitrile and 2.32 g (25 mmol) of aniline at 65° C. The crude product is purified by vacuum flash chromatography (heptane) to give 2.8 g of colorless oil in a 48% yield based on the aniline.

EXAMPLE 5

1-Phenoxy-2,2,6,6-tetramethylpiperidine

This example shows the effect of temperature on the reaction. Example 4 is repeated at room temperature.

The procedure of Example 1 is repeated using 15.6 g (100 mmol) of 1-oxyl-2,2,6,6-tetramethylpiperidine, 3.92 g (38 mmol) of tert-butyl nitrite, 0.13 g (1.3 mmol) of copper(II) fluoride, 120 mL of acetonitrile and 2.32 g (25 mmol) of aniline at ambient temperature for 72 hours. The crude product is purified by vacuum flash chromatography (heptane) to give 3.0 g of colorless oil in a 52% yield based on the aniline.

EXAMPLE 6

1-Phenoxy-2,2,6,6-tetramethylpiperidine

This experiment shows the effect of having a 2 molar excess of aniline and 0.5 mol % of copper(II) fluoride catalyst.

The procedure of Example 1 is repeated using 3.9 g (25 mmol) of 1-oxyl-2,2,6,6-tetramethylpiperidine, 7.84 g (76 mmol) of tert-butyl nitrite, 25 mg (0.25 mmol) of copper(II) fluoride, 120 mL of acetonitrile and 4.65 g (50 mmol) of aniline at 65° C. The crude product is purified by vacuum flash chromatography (heptane) to give 3.8 g of colorless oil in a 66% yield based on nitroxyl.

EXAMPLE 7

1-Phenoxy-2,2,6,6-tetramethylpiperidine

This example shows the effect of temperature on the instant process. Example 6 is repeated at room temperature.

The procedure of Example 1 is repeated using 3.9 g (25 mmol) of 1-oxyl-2,2,6,6-tetramethylpiperidine, 7.84 g (76 mmol) of tert-butyl nitrite, 25 mg (0.25 mmol) of copper(II) fluoride, 120 mL of acetonitrile and 4.65 g (50 mmol) of aniline at ambient temperature for 72 hours. The crude product is purified by vacuum flash chromatography (heptane) to give 2.5 g of colorless oil in a 43% yield based on nitroxyl.

EXAMPLE 8

1-Phenoxy-2,2,6,6-tetramethyl-4-hydroxypiperidine

This example shows the effect of excess nitroxyl and 5 mol % copper(II) fluoride catalyst.

The procedure of Example 1 is repeated using 17.2 g (100 mmol) of 1-oxyl-2,2,6,6-tetramethyl-4-hydroxypiperidine, 3.92 g (38 mmol) of tert-butyl nitrite, 0.13 g (1.3 mmol) of copper(II) fluoride, 120 mL of acetonitrile and 2.32 g (25 mmol) of aniline at 65° C. The crude product is purified by vacuum flash chromatography (25 ethyl acetate/heptane) to give 3.4 g of colorless oil in a 55% yield based on the aniline.

EXAMPLE 9

1-(2-Nitro-4-trifluoromethylphenoxy)-2,2,6,6-tetramethylpiperidine

The procedure of Example 1 is repeated using 3.9 g (25 mmol) of 1-oxyl-2,2,6,6-tetramethyl-4-hydroxypiperidine, 7.84 g (76 mmol) of tert-butyl nitrite, 25 mg (0.25 mmol) of copper(II) fluoride, 120 mL of acetonitrile and 10.3 g (50 mmol) of 2-nitro-4-trifluoromethylaniline at 65° C. The crude product obtained is purified by vacuum flash chromatography (heptane) to give 6.0 g of light yellow crystals melting at 54–55° C., a 68.9% yield based on nitroxyl. The structure is confirmed by $^1$Hnmr, mass spectroscopy and elemental analyses.

$^1$Hnmr (CDCl$_3$) (300.08 MHz) d 1.94, 1.76, 1.62 (overlapping m, CH$_2$, 4H), 1.30 (s, CH$_3$, 6H), 1.07 (s, CH$_3$, 6H), 4.05 (m, CH, 1H), 7.22 (overlapping m, CH, 4H), 6.87 (tt, CH, 1H $^3J_{HH'}$=6.8 Hz, $^4J_{HH''}$=1.6 Hz); MS m/s 249. Analysis: Calcd for C$_{16}$H$_{21}$F$_3$N$_2$O$_3$: C, 55.4; H, 6.1; N, 8.1. Found: C, 55.4; H, 6.2; N, 8.1.

EXAMPLE 10

1-(2,4-Dibromophenoxy)-4-hydroxy-2,2,6,6-tetramethylpiperidine

The procedure of Example 1 is repeated using 12.8 g (74 mmol) of 1-oxyl-2,2,6,6-tetramethyl-4-hydroxypiperidine, 14.23 g (138 mmol) of tert-butyl nitrite, 0.73 g (0.74 mmol) of copper(II) fluoride, 200 mL of pyridine and 8.56 g (92 mmol) of 2,4-dibromoaniline at 65° C. The crude product obtained is purified by vacuum flash chromatography (5% ethyl acetate/heptane) to give 17 g of the title compound as a yellowish solid solid in 63.5% yield. The structure is confirmed by $^1$Hnmr analysis.

$^1$Hnmr (C$_6$D$_6$) (300.08 MHz) d 1.62 1.95 (overlapping m, CH$_2$, 4H), 1.01 (s, CH$_3$, 6H) 1.34 (s, CH$_3$, 6H), 4.09 (m, OCH, 1H), 7.29 (dd, CH, 1H, $^3J_{HH'}$=8.9 Hz, $^4J_{HH'}$=2.3 Hz), 7.43 (d, CH, 1H, $^3J_{HH'}$=9.4 Hz), 7.58 (d, CH, 1H, $^4J_{HH'}$=2.3 Hz).

EXAMPLE 11

1-Phenoxy-2,2,6,6-tetramethylpiperidine

This example shows the use of a mixture of acetonitrile and pyridine as the reaction medium.

The process of Example 1 is repeated using 3.9 g (25 mmol) of 1-oxyl-2,2,6,6-tetramethylpiperidine, 7.84 g (76 mmol) of tert-butyl nitrite, 25 mg (0.25 mmol) of copper(II) fluoride in a mixture of 100 mL of acetonitrile/20 mL of pyridine and 4.65 g (50 mmol) of aniline in 10 mL of acetonitrile at 70° C. The crude product obtained is purified by vacuum flash chromatography (heptane) to give 4.9 g of the title compound as a colorless oil in 84.5% yield.

EXAMPLE 12

1-Phenoxy-2,2,6,6-tetramethylpiperidine

This example shows the use of pyridine alone as the reaction medium.

The procedure of Example 1 is again repeated using 3.9 g (25 mmol) of 1-oxyl-2,2,6,6-tetramethylpiperidine, 7.84 g (76 mmol) of tert-butyl nitrite, 25 mg (0.25 mmol) of copper(II) fluoride in a mixture of 120 mL of pyridine and 4.65 g (50 mmol) of aniline at 70° C. The crude product obtained is purified by vacuum flash chromatography (heptane) to give 4.8 g of the title compound as a colorless oil in 82.8% yield.

EXAMPLE 13

1-Phenoxy-2,2,6,6-tetramethylpiperidine

This example shows the use of equal molar equivalents of nitroxyl radical and aniline.

The procedure of Example 1 is repeated using 3.9 g (25 mmol) of 1-oxyl-2,2,6,6-tetramethylpiperidine, 7.84 g (76 mmol) of tert-butyl nitrite, 25 mg (0.25 mmol) of copper(II) fluoride in a mixture of 120 mL of pyridine and 2.32 g (25 mmol) of aniline at 70° C. The crude product formed is purified by vacuum flash chromatography (heptane) to give 4.5 g of the title compound as a colorless oil in 77.6% yield.

EXAMPLE 14

1-(2-Nitro-4-chlorophenoxy)-2,2,6,6-tetramethylpiperidine

The procedure of Example 1 is repeated using 3.9 g (25 mmol) of 1-oxyl-2,2,6,6-tetramethylpiperidine, 7.84 g (76 mmol) of tert-butyl nitrite, 25 mg (0.25 mmol) of copper(II) fluoride, 120 mL of pyridine and 8.6 g (50 mmol) of 2-nitro-4-chloroaniline at 70° C. The crude product obtained is purified by vacuum flash chromatography (heptane) to give 5.2 g of the title compound as a light yellow oil in 66.7% yield. The structure is confirmed by $^1$Hnmr and mass spectroscopy analyses.

$^1$Hnmr ($C_6D_6$) (499.84 MHz) d 1.35, 1.28, 0.95 (overlapping m, $CH_2$, 6H), 0.84 (s, $CH_3$, 6H), 1.14 (s, $CH_3$, 6H), 6.95 (dd, CH, 1H, $^3J_{HH'}$=8.9 Hz, $^4J_{HH''}$=1.9 Hz), 7.44 (d, CH, $^3J_{HH'}$=8.9 Hz), 7.51 (d, CH, 1H, $^4J_{HH''}$=1.9 Hz); MS m/z 312. Analysis: Calcd for $C_{15}H_{21}ClN_2O_3$: C, 57.6; H, 6.7; N, 8.9. Found: C, 57.3; H, 6.5; N, 8.9.

EXAMPLE 15

1-(2,4-Dibromophenoxy)-2,2,6,6-tetramethylpiperidine

The procedure of Example 1 is repeated using 1.95 g (12.5 mmol) of 1-oxyl-2,2,6,6-tetramethylpiperidine, 3.92 g (38 mmol) of tert-butyl nitrite, 12.5 mg (0.125 mmol) of copper (II) fluoride, 120 mL of pyridine and 6.30 g (25 mmol) of 2,4-dibromoaniline at 70° C. The crude product obtained is purified by vacuum flash chromatography (heptane) to give 3.34 g of the title compound as a light yellow oil in 68.5% yield. The structure is confirmed by $^1$Hnmr analysis.

$^1$Hnmr ($C_6D_6$) (499.84 MHz) d 1.38, 1.25, 1.11 (overlapping m, $CH_2$, 6H), 0.86 (s, $CH_3$, 6H), 1.22 (s, $CH_3$, 6H), 7.07 (dd, CH, 1H, $^3J_{HH'}$=8.9 Hz, $^4J_{HH''}$=1.9 Hz), 7.23 (d, CH, 1H, $^3J_{HH'}$=8.9 Hz), 7.52 (d, CH, 1H, $^4J_{HH''}$=1.9 Hz).

EXAMPLE 16

1-(4-Benzoylphenoxy)-2,2,6,6-tetramethylpiperidine

The procedure of Example 1 is repeated using 1.95 g (12.5 mmol) of 1-oxyl-2,2,6,6-tetramethylpiperidine, 3.92 g (38 mmol) of tert-butyl nitrite, 12.5 mg (0.125 mmol) of copper (II) fluoride, 120 mL of pyridine and 4.93 g (25 mmol) of 4-aminobenzophenone in 40 mL of pyridine at 70° C. The crude product obtained is purified by vacuum flash chromatography (heptane) to give 3.40 g of the title compound as a light yellow oil in 80.6% yield. The structure is confirmed by $^1$Hnmr, elemental and mass spectrographic analysis.

$^1$Hnmr ($CDCl_3$) (300.08 MHz) d 1.63, 1.44 (overlapping m, $CH_2$, 6H), 1.03 (s, $CH_3$, 6H), 1.26 (s, $CH_3$, 6H), 7.48, 7.55 (overlapping m, CH, 4H), 7.78 (d, 1H, $^3J_{HH'}$=6.8 Hz, $^4J_{HH''}$=1.6 Hz); MS m/z 249. Analysis: Calcd for $C_{22}H_{27}NO_2$: C, 78.3; H, 8.1; N, 4.2. Found: C, 78.1; H, 8.0; N, 4.2.

EXAMPLE 17

1-Phenoxy-2,2,6,6-tetramethylpiperidine

This example shows the use of an aqueous diazotization with sodium nitrite and hydrochloric acid in place of tert-butyl nitrite in organic medium.

Into a solution of 5 g of water and 15.3 g (150 mmol) of concentrated hydrochloric acid is added dropwise 4.60 g (50 mmol) of aniline. The temperature of the reaction mixture during the addition step is kept under 40° C. After the addition is complete, the reaction mixture is heated to 70° C. for one hour. The reaction mixture is then cooled to 0° to 5° C. followed by a dropwise addition of an aqueous solution of 3.45 g (50 mmol) of sodium nitrite in 10 mL of water. The addition time is 20 minutes while the reaction temperature is maintained at 0° to 5° C. The reaction mixture is transferred to a cold-jacketed addition funnel and is then added dropwise into a solution of 3.9 g (25 mmol) of 1-oxyl-2,2,6,6-tetramethylpiperidine, 25 mg (0.25 mmol) of copper(II) fluoride in 120 mL of pyridine at 70° C. Evolution of nitrogen is observed during the addition. After the addition is complete, the reaction mixture is kept at 70° C. for another 30 minutes followed by cooling to ambient temperature. The reaction mixture is concentrated to a thick oil. The crude product is purified by vacuum flash chromatography (heptane) to give 3.97 g of the title as a colorless oil in 68.4% yield.

EXAMPLE 18

1-Phenoxy-2,2,6,6-tetramethylpiperidine

This example shows the use of various other transition metal catalysts for preparing the title compound.

When the procedure of Example 1 is repeated by replacing copper(II) fluoride with an equivalent amount of the following catalysts:
copper(I) chloride (72.4% yield);
cobalt(II) acetate (67% yield);
manganese(II) chloride;
ferrous chloride;
ferric chloride;
titanium (III) chloride;
the title compound is prepared in good yield.

EXAMPLE 19

1-Phenoxy-2,2,6,6-tetramethylpiperidine

This example shows the use of a two molar excess of aniline and pyridine, but first without copper(II) catalyst. No reaction occurs till the copper catalyst is added.

Into a solution of 3.9 g (25 mmol) of 1-oxyl-2,2,6,6-tetramethylpiperidine and 3.92 g (39 mmol) of tert-butyl nitrite in 120 mL of pyridine at 65–70° C. is added a solution of 2.32 g (25 mmol) of aniline. During the addition, no evolution of nitrogen is observed. After 1.5 hours no product is observed by thin layer chromatography. Into the reaction mixture at 65–70° C., 25 mg (0.25 mmol) of copper(II) fluoride is now added and a vigorous eveolution of nitrogen is observed. After 15 minutes, the reaction mixture is concentrated and purified by vacuum flash chromatography (heptane) to give 2.4 g of the title compound as a colorless oil in 41.4% yield.

EXAMPLE 20

1-Phenoxy-2,2,6,6-tetramethylpiperidine

This example shows the substitution of pyridine by diethylamine as solvent with two molar excess of aniline and 0.5 mole % copper(II) catalyst.

The procedure of Example 1 is repeated using 1.95 g (12.5 mmol) of 1-oxyl-2,2,6,6-tetramethylpiperidine, 3.90 g (38 mmol) of tert-butyl nitrite, 12.5 mg (0.125 mmol) of copper (II) fluoride, 120 mL of triethylamine and 2.30 g (25 mmol) of aniline at 70° C. The crude product is purified by vacuum flash chromatography (heptane) to give 2.3 g of the title compound as a colorless oil in a 65.6% yield.

EXAMPLE 21

1-Phenoxy-2,2,6,6-tetramethylpiperidine

This example shows the use of a three molar excess of aniline and 0.03 mole % cobalt(II) catalyst and pyridine.

The procedure of Example 1 is repeated using 1.95 g (12.5 mmol) of 1-oxyl-2,2,6,6-tetramethylpiperidine, 4.12 g (40 mmol) of tert-butyl nitrite, 7.5 mg (0.0125 mmol) of (S,S)-(+)-N,N-bis(3,5-di-tert-butylsalicylidene)-1,2-cyclohexanediaminocobalt(II) in a mixture of 120 mL of pyridine and 3.48 g (37.5 mmol) of aniline at 70° C. The crude product is purified by vacuum flash chromatography (heptane) to give 2.67 g of the title compound as a colorless oil in a 91.8% yield.

EXAMPLE 22

1-Phenoxy-2,2,6,6-tetramethylpiperidine

This example shows the use of a three molar excess of aniline and 0.03 mole % cobalt(II) catalyst and pyridine.

The procedure of Example 1 is repeated using 1.95 g (12.5 mmol) of 1-oxyl-2,2,6,6-tetramethylpiperidine, 4.12 g (40 mmol) of tert-butyl nitrite, 4.01 mg (0.0125 mmol) of N,N-bis(salicylidene)ethylenediaminocobalt(II) in a mixture of 120 mL of pyridine and 3.48 g (37.5 mmol) of aniline at 70° C. The crude product is purified by vacuum flash chromatography (heptane) to give 2.64 g of the title compound as a colorless oil in a 90.7% yield.

EXAMPLE 23

1-Phenoxy-2,2,6,6-tetramethylpiperidine

This example shows the use of a two molar excess of aniline and 0.03 mole % cobalt(II) catalyst and chlorobenzene.

The procedure of Example 1 is repeated using 1.95 g (12.5 mmol) of 1-oxyl-2,2,6,6-tetramethylpiperidine, 3.09 g (30 mmol) of tert-butyl nitrite, 7.5 mg (0.0125 mmol) of (S,S)-(+)-N,N-bis(3,5-di-tert-butylsalicylidene)-1,2-cyclohexanediaminocobalt(II)in a mixture of 120 mL of chlorobenzene and 2.33 g (25 mmol) of aniline at 70° C. The crude product is purified by vacuum flash chromatography (heptane) to give 2.20 g of the title compound as a colorless oil in a 75.6% yield.

EXAMPLE 24

1-Phenoxy-2,2,6,6-tetramethylpiperidine

The procedure of Example 21 is repeated, but substituting for the (S,S)-(+)-N,N-bis(3,5-di-tert-butylsalicylidene)-1,2-cyclohexanediaminocobalt(II) any one of the following catalysts:
cobalt(II) phthalocyanine;
5,10,15,20-tetraphenyl-21H,23H-porphine cobalt(II);
5,10,15,20-tetrakis(4-methoxyphenyl)-21H,23H-porphine cobalt(II); or
2,3,7,8,12,13,17,18-octaethyl-21H,23H-porphine cobalt(II).

EXAMPLE 25

1-Phenoxy-2,2,6,6-tetramethylpiperidine

This example shows the use of a two molar excess of aniline, 0.5 mole % of copper(II) chloride and acetonitrile.

The procedure of Example 1 is repeated using 3.9 g (25 mmol) of 1-oxyl-2,2,6,6-tetramethylpiperidine, and 7.84 g (76 mmol) of tert-butyl nitrite, 24 mg (0.25 mmol) of copper(II) chloride, 120 mL of acetonitrile and 4.65 g (50 mmol) of aniline at 65° C. The crude product is purified by vacuum flash chromatography (heptane) to give 4.2 g of the title compound as a colorless oil in a 72.4% yield.

EXAMPLE 26

1-Phenoxy-2,2,6,6-tetramethylpiperidine

This example shows the use of a two molar excess of aniline, 0.5 mole % of cobalt(II) acetate and acetonitrile.

The procedure of Example 1 is repeated using 3.9 g (25 mmol) of 1-oxyl-2,2,6,6-tetramethylpiperidine, and 7.84 g (76 mmol) of tert-butyl nitrite, 44 mg (0.25 mmol) of cobalt(II) acetate, 120 mL of acetonitrile and 4.65 g (50 mmol) of aniline at 65° C. The crude product is purified by vacuum flash chromatography (heptane) to give 3.9 g of the title compound as a colorless oil in a 67.2% yield.

EXAMPLE 27

1-Phenoxy-2,2,6,6-tetramethylpiperidine

This example shows the use of a two molar excess of aniline, 0.5 mole % of manganese(II) chloride and acetonitrile.

The procedure of Example 1 is repeated using 3.9 g (25 mmol) of 1-oxyl-2,2,6,6-tetramethylpiperidine, and 7.84 g (76 mmol) of tert-butyl nitrite, 31 mg (0.25 mmol) of manganese(II) chloride, 120 mL of acetonitrile and 4.65 g (50 mmol) of aniline at 70° C. The crude product is purified by vacuum flash chromatography (heptane) to give 3.6 g of the title compound as a colorless oil in a 62.1% yield.

EXAMPLE 28

1-Phenoxy-4-benzoyloxy-2,2,6,6-tetramethylpiperidine

The procedure of Example 1 is repeated using 5.79 g (0.021 mmol) of 1-oxyl-4-benzoyloxy-2,2,6,6-tetramethylpiperidine, 5.05 g (49 mmol) of tert-butyl nitrite, 12.6 mg (0.125 mmol) of copper(II) fluoride, 120 mL of pyridine and 3.91 g (42 mmol) of aniline at 70° C. The crude product obtained is purified by vacuum flash chromatography (heptane) to give 4.10 g of the title compound as a yellowish oil in 55.3% yield. The structure is confirmed by mass spectrographic analysis. MS [M+1]354.

EXAMPLE 29

N-Phenoxy-di-tert-butylamine

The procedure of Example 1 is repeated using 1.80 g (12.5 mmol) of di-tert-butyl nitroxide, 3.09 g (38 mmol) of tert-butyl nitrite, 7.6 mg (0.125 mmol) of (S,S)-(+)-N,N-bis(3,5-di-tert-butylsalicylidene)-1,2-cyclohexanediaminocobalt(II), 120 mL of pyridine and 2.30 g (25 mmol) of aniline at 70° C. The crude product obtained is purified by vacuum flash chromatography (heptane) to give 2.21 g of the title compound as a colorless oil in 80.3% yield. The structure is confirmed by $^1$Hnmr and elemental analysis.

$^1$Hnmr (CDCl$_3$) (300.08 MHz) d 1.26 (s, C(CH$_3$)$_3$, 18H), 7.22 (overlapping m, 4H), 6.84 (tt, 1H, $^3J_{HH'}$=6.8 Hz, $^4J_{HH''}$=1.6 Hz). Analysis: Calcd for C$_{14}$H$_{23}$NO: C, 75.9; H, 10.5; N, 6.3. Found: C, 75.4; H, 9.8; N, 6.3.

EXAMPLE 30

2,4-Bis[N-butyl-N-(1-phenoxy-2,2,6,6-tetramethylpiperidin-4-yl)amino]-6-chloro-s-triazine The procedure of Example 1 is repeated using 3.89 g (6.90 mmol) of 2,4-bis[N-butyl-N-(1-oxyl-2,2,6,6-tetramethylpiperidin-4-yl)amino]-6-chloro-s-triazine, 3.29 g (32 mmol) of tert-butyl nitrite, 4.2 mg (0.0069 mmol) of (S,S)-(+)-N,N-bis(3,5-di-tert-butylsalicylidene)-1,2-cyclohexanediaminocobalt(II), 120 mL of pyridine and 2.56 g (27.6 mmol) of aniline at 70° C. The crude product obtained is purified by vacuum flash chromatography (heptane) to give 3.0 g of the title compound as an off-white solid in 60.5% yield.

EXAMPLE 31

2,4-Bis{N-butyl-N-[1-(2,4-dibromophenoxy)-2,2,6,6-tetra-methylpiperidin-4-yl]amino}-6-[N,N-bis(2-ethylhexyl)amino]-s-triazine The procedure of Example 1 is repeated using 10 g (13 mmol) of 2,4-bis[N-butyl-N-(1-oxyl-2,2,6,6-tetramethylpiperidin-4-yl)amino]-6-[N,N-bis(2-ethylhexyl)amino]-s-triazine, 6.18 g (60 mmol) of tert-butyl nitrite, 7.8 mg (0.013 mmol) of (S,S)-(+)-N,N-bis(3,5-di-tert-butylsalicylidene)-1,2-cyclohexanediaminocobalt(II), 140 mL of pyridine and 13.05 g (52 mmol) of 2,4-dibromoaniline at 85° C. The crude product obtained is purified by vacuum flash chromatography (2% ethyl acetate/heptane) to give 7 g of the title compound as a light yellow solid in 43.4% yield. The structure is confirmed by $^1$Hnmr and elemental analysis.

$^1$Hnmr (CDCl$_3$) (499.84 MHz) d 0.89 (t, CH$_3$, 12H), 0.97 (t, CH$_3$, 6H), 1.03 (s, CH$_3$, 12H), 1.44 (s, CH$_3$, 12H), 1.28 (overlapping m, CH$_2$, 24H), 1.82, 1.60 (overlapping m, CH$_2$, 8H), 3.35 (overlapping dd, NCH$_2$, 4H), 3.58 (t, NCH$_2$, 4H), 5.26 (m, NCH, 2H), 7.30 (dd, 2H, $^3J_{HH'}$=8.79 Hz, $^4J_{HH'}$=2.29 Hz), 7.59 (d, 2H, $^4J_{HH'}$=2.32 Hz), 7.48 (d, 2H, $^3J_{HH'}$=8.91 Hz). Analysis: Calcd for C$_{57}$H$_{92}$Br$_4$N$_8$O$_2$: C, 55.2; H, 7.5; N, 9.0. Found: C, 55.8; H, 7.3; N, 8.7.

EXAMPLE 32

2,4-Bis[N-butyl-N-(1-phenoxy-2,2,6,6-tetra-methylpiperidin-4-yl)amino]-6-[N,N-bis(2-ethylhexyl)amino]-s-triazine The procedure of Example 1 is repeated using 5 g (6.5 mmol) of 2,4-bis[N-butyl-N-(1-oxyl-2,2,6,6-tetramethylpiperidin-4-yl)amino]-6-[N,N-bis(2-ethylhexyl)amino]-s-triazine, 3.09 g (30 mmol) of tert-butyl nitrite, 3.9 mg (0.0065 mmol) of (S,S)-(+)-N,N-bis(3,5-di-tert-butylsalicylidene)-1,2-cyclohexanediaminocobalt(II), 120 mL of pyridine and 2.42 g (26 mmol) of aniline at 75° C. The crude product obtained is purified by vacuum flash chromatography (2% ethyl acetate/heptane) to give 5 g of the title compound as a reddish oil in 83.3% yield. The structure is confirmed by $^1$Hnmr and elemental analysis.

$^1$Hnmr (CDCl$_3$) (499.84 MHz) d 0.89 (t, CH$_3$, 12H), 0.98 (t, CH$_3$, 6H), 1.07 (s, CH$_3$, 12H), 1.54 (s, CH$_3$, 12H), 1.27 (overlapping m, CH$_2$, 24H), 1.82, 1.64 (overlapping m, CH$_2$, 8H), 3.36 (overlapping dd, NCH$_2$, 4H), 3.61 (t, NCH$_2$, 4H), 5.25 (m, NCH, 2H), 6.87 (dd, 2H, $^3J_{HH'}$=8.79 Hz, $^4J_{HH'}$=2.29 Hz), 7.21 (d, 2H, $^4J_{HH'}$=2.32 Hz), 7.51 (d, 2H, $^3J_{HH'}$=8.91 Hz). Analysis: Calcd for C$_{57}$H$_{96}$N$_8$O$_2$: C, 73.9; H, 10.5; N, 12.1. Found: C, 74.3; H, 10.2; N, 11.9.

EXAMPLE 33

1-(3,5-di-tert-butylphenoxy)-2,2,6,6-tetramethylpiperidine

The procedure of Example 1 is repeated using 1.50 g (9.6 mmol) of 1-oxyl-2,2,6,6-tetramethylpiperidine, 2.38 g (24 mmol) of tert-butyl nitrite, 5.8 mg (0.0096 mmol) of (S,S)-(+)-N,N-bis(3,5-di-tert-butylsalicylidene)-1,2-cyclohexanediaminocobalt(II), 90 mL of pyridine and 3.93 g (19.2 mmol) of 3,5-di-tert-butylaniline at 70° C. The crude product obtained is purified by vacuum flash chromatography (heptane) to give 2.8 g of the title compound as an off-white solid in 84.8% yield. The structure is confirmed by $^1$Hnmr and elemental analysis.

$^1$Hnmr (CDCl$_3$) (499.84 MHz) 1.43, 1.61 (overlapping m, CH$_2$, 6H), 1.02 (s, CH$_3$, 6H), 1.24 (s, CH$_3$, 6H), 1.31 (s, CH$_3$, 18H), 6.88 (t, CH, 1H), 7.03 (d, OCCH, 1H, $^4J_{HH'}$=1.9 Hz). Analysis: Calcd for C$_{23}$H$_{39}$NO: C, 79.9; H, 11.4; N, 4.1. Found: C, 80.0; H, 11.7; N, 4.0.

EXAMPLE 34

1-(Pyridin-3-yloxy)-2,2,6,6-tetramethylpiperidine

The procedure of Example 1 is repeated using 1.95 g (12.5 mmol) of 1-oxyl-2,2,6,6-tetramethylpiperidine, 3.90 g (38 mmol) of tert-butyl nitrite, 7.6 mg (0.0125 mmol) of (S,S)-(+)-N,N-bis(3,5-di-tert-butylsalicylidene)-1,2-cyclohexanediaminocobalt(II), 120 mL of pyridine and 2.35 g (25 mmol) of 3-aminopyridine at 70° C. The crude product obtained is purified by vacuum flash chromatography (heptane) to give 1.5 g of the title compound as a colorless oil in 50.8% yield. The structure is confirmed by $^1$Hnmr and mass spectrographic analyses.

$^1$Hnmr (C$_6$D$_6$) (300.08 MHz) 1.07, 1.20, 1.29 (overlapping m, CH$_2$, 6H), 0.89 (s, CH$_3$, 6H), 1.07 (s, CH$_3$, 6H), 6.71 (ddd, $^3J_{HH'}$=8.42 Hz, $^3J_{HH'}$=4.56 Hz, $^5J_{HH'}$=0.61 Hz), 7.26 (ddd, $^3J_{HH'}$=8.37 Hz, $^4J_{HH''}$=2.76 Hz, $^4J_{HH'}$=1.34 Hz), 8.22 (dd, $^3J_{HH'}$=2.37 Hz, $^4J_{HH'}$=1.37 Hz), 8.80 (d, $^4J_{HH'}$=2.74 Hz); MS m/z 249.

EXAMPLE 35

1-(2-Nitro-4-chlorophenoxy)-2,2,6,6-tetramethyl-4-hydroxypiperidine

The procedure of Example 1 is repeated using 4.31 g (25 mmol) of 1-oxyl-2,2,6,6-tetramethyl-4-hydroxypiperidine, 7.73 g (75 mmol) of tert-butyl nitrite, 25 mg (0.25 mmol) of copper(II) flouride, 70 mL of pyridine and 5.61 g (32.5 mmol) of 4-chloro-2-nitroaniline at 70° C. The crude product obtained is purified by vacuum flash chromatography (70:30/heptane:ethyl acetate) to give 4.28 g of the title compound in 84.8% yield as a light yellow solid melting at 124–125.5° C. The structure is confirmed by $^1$Hnmr and elemental analysis.

$^1$Hnmr (CDCl$_3$) (499.85 MHz) 1.06 (s, 6H), 1.35 (s, 6H), 1.64 (dd, 2H), 1.98 (dd, 2H), 4.12 (tt. 1H), 7.43 (dd, 1H), 7.83 (dd, 1H), 7.87 (dd, 1H). Analysis: Calcd for C$_{15}$H$_{21}$ClN$_2$O$_4$: C, 54.8; H, 6.4; N, 8.5. Found: C, 54.7; H, 6.2; N, 8.5.

EXAMPLE 36

4,4'-Bis(2,2,6,6-tetramethylpiperidin-1-yloxy)benzophenone

The procedure of Example 1 is repeated using 1.95 g (12.5 mmol) of 1-oxyl-2,2,6,6-tetramethylpiperidine, 6.19 g (60 mmol) of tert-butyl nitrite, 7.6 mg (0.0125 mmol) of (S,S)-(+)-N,N-bis(3,5-di-tert-butylsalicylidene)-1,2-cyclohexanediaminocobalt(II), 80 mL of pyridine and 5.30 g (25 mmol) of 4,4'-diaminobenzophenone at 70° C. The crude product obtained is purified by vacuum flash chromatography (1% ethyl acetate in heptane) to give 0.6 g of the title compound as a yellow solid in 9.17% yield. The structure is confirmed by $^1$Hnmr and mass spectrographic analysis.

$^1$Hnmr (CDCl$_3$) (300.08 MHz) 1.39, 1.28, 1.25 (overlapping m, CH$_2$, 12H), 0.97 (s, CH$_3$, 12H), 1.13 (s, CH$_3$, 12H), 7.13 (d, 4H, $^3J_{HH'}$=9.0 Hz), 7.86 (d, 4H, $^3J_{HH'}$=9.0 Hz); MS[M+1] 493.

EXAMPLE 37

Di(1-phenoxy-2,2,6,6-tetramethylpiperidin-4-yl) Sebacate

The procedure of Example 1 is repeated using 23.32 g (240 mmol) of bis(1-oxyl-2,2,6,6-tetramethylpiperidin-4-yl) sebacate, 30.9 g (300 mmol) of tert-butyl nitrite, 35.5 mg (0.059 mmol) of (S,S)-(+)-N,N-bis(3,5-di-tert-butylsalicylidene)-1,2-cyclohexanediaminocobalt(II), 120 mL of pyridine and 22.32 g (240 mmol) of aniline at 70° C. A total of 10 g of the 47 g of crude product is purified by vacuum flash chromatography (1% ethyl acetate in heptane) to give 4.0 g of the title compound as a yellowish solid in 47.9% yield. The structure is confirmed by $^1$Hnmr, elemental and mass spectrographic analyses.

$^1$Hnmr (C$_6$D$_6$) (300.08 MHz) 1.63, 1.73, 1.95 (overlapping m, CH$_2$, 12H), 1.06 (s, CH$_3$, 12H), 1.34 (s, CH$_3$, 12H), 2.30 (t, OCOCH$_2$, $^3J_{HH'}$=7.7 Hz), 5.13 (m, CHOCO, 2H), 7.21 (d, CH, 4H, $^3J_{HH'}$=6.8 Hz), 7.19 (d, CH, 4H, $^3J_{HH'}$=7.29 Hz), 6.87 (tt, CH, 2H, $^3J_{HH'}$=6.8 Hz, $^4J_{HH''}$=1.6 Hz); MS[M+1] m/z 665. Analysis: C$_{40}$H$_{60}$N$_2$O$_6$: C, 72.3; H, 9.1; N, 4.2. Found: C, 72.3; H, 9.3; N, 4.5.

EXAMPLE 38

1-Phenoxy-2,2,6,6-tetramethylpiperidine

This example shows the use of 1 molar excess aniline, pyridine and 0.03 mole % of gold(I) catalyst.

The procedure of Example 1 is repeated using 1.95 g (12.5 mmol) of 1-oxyl-2,2,6,6-tetramethylpiperidine, 3.09 g (30 mmol) of tert-butyl nitrite, 2.9 mg (0.0125 mmol) of gold(I) chloride in a mixture of 80 mL of pyridine and 2.33 g (25 mmol) of aniline at 70° C. The crude product obtained is purified by vacuum flash chromatography (heptane) to give 2.58 g of the title compound as a colorless oil in 88.6% yield.

EXAMPLE 39

1-Phenoxy-2,2,6,6-tetramethylpiperidine

This example shows the use of 2 molar excess aniline, 2 molar pyridine, chlorobenzene and 0.03 mole % of cobalt(II) catalyst.

The procedure of Example 1 is repeated using 1.95 g (12.5 mmol) of 1-oxyl-2,2,6,6-tetramethylpiperidine, 3.09 g (30 mmol) of tert-butyl nitrite, 7.5 mg (0.0125 mmol) of (S,S)-(+)-N,N-bis(3,5-di-tert-butylsalicylidene)-1,2-cyclohexanediaminocobalt(II), 120 mL of chlorobenzene and 2.30 g (25 mmol) of aniline at 70° C. The crude product obtained is purified by vacuum flash chromatography (heptane) to give 2.53 g g of the title compound as a colorless oil in 86.6% yield.

EXAMPLE 40

1-(Phthalimid-4-yloxy)-4-hydroxy-2,2,6,6-tetramethylpiperidine

The procedure of Example 1 is repeated using 4.31 g (25 mmol) of 1-oxyl-4-hydroxy-2,2,6,6-tetramethylpiperidine, 5.16 g (50 mmol) of tert-butyl nitrite, 15 mg (0.025 mmol) of (R,R)-(+)-N,N-bis(3,4-di-tert-butylsalicylidene)-1,2-cyclohexanediaminocobalt(II), 125 mL of pyridine and 4.86 g (30 mmol) of 4-aminophthalimide at 75° C. to give the title compound, MS 318.

EXAMPLE 41

1-Phenoxy-3-carboxy-2,2,5,5-tetramethylpyrrolidine

The title compound is prepared by the procedure of Example 21 by substituting 1-oxyl-3-carboxy-2,2,5,5-tetramethylpyrrolidine in place of 1-oxyl-2,2,6,6-tetramethylpiperidine.

EXAMPLE 42

4,4'-Bis[(4-hydroxy-2,2,6,6-tetramethylpiperidin-1-yl)oxy]diphenylmethane

The procedure of Example 1 is repeated using 8.61 g (50 mmol) of 1-oxyl-2,2,6,6-tetramethyl-4-hydroxypiperidine, 7.73 g g (75 mmol) of tert-butyl nitrite, 30 mg (0.05 mmol) of (R,R)-(−)-N,N-bis(3,5-di-tert-butylsalicylidene)-1,2-cyclohexanediaminocobalt(II), 100 mL of pyridine and 4.96 g (25 mmol) of 4,4'-methylenedianiline in 25 mL of pyridine at 70° C. The residue is triturated with 300 mL of isopropanol and the resultant solid is collected by filtration. The crude product obtained is purified by vacuum flash chromatography (10% ethyl acetate/heptane followed by 50% ethyl acetate/heptane) followed by recrystallization from acetonitrile (15 mL) to give 0.18 g of a light yellow solid: MS m/z 510.

The bis(trimethylsilyl)trifluoroacetamide derivatived sample [bis(trimethylsilyl)-derivative of the two hydroxyl substituents] showed the appropriate molecular ion in the mass spectrum at 654.

EXAMPLE 43

Molding grade polypropylene is dry blended with test additives and then melt compounded into pellets. The pelletized fully formulated resin is then injection molded into test specimens using a Boy 50M laboratory model injection molder.

Test plaques are mounted in metal frames and exposed in an Atlas Ci65 Xenon Arc Weather-Ometer with intermittent light/dark cycles and water spray following ASTM G26 test procedure. Specimens are tested at periodic intervals for changes in tensile properties. Failure in this test is determined by the observation of the loss of tensile properties. The longer it takes for the loss in properties to occur, the more effective is the stabilizer system.

The test samples containing the instant compounds of Examples 1, 8, 9, 14, 15 and 16 exhibit good light stabilization properties.

Raw Materials

Wax samples are supplied by the Candle-Lite Corporation. These samples contain dyes and fragrances.

The UV absorbers and hindered amine stabilizers are obtained from the Ciba Speciality Chemicals Corporation.

Sample Preparation

The wax samples obtained from the Candle-Lite Corporation already contain a dye and a fragrance (scent). In these cases, the wax is melted and the appropriate stabilizer(s) is (are) added and dissolved in the molten wax. The stabilized wax is then poured into five (5) 44 mm diameter aluminum pans giving five (5) wax disks.

Sample Exposure

Triplicate samples of each disk are exposed under a bank of six (6) cool-white fluorescent lamps (40 watts) or under a bank of six (6) UV lamps having a wavelength of 368 nm with the test samples being twelve (12) inches (30.48 cm) below the lamps.

Dye color fade (or color change) is measured by a Macbeth ColorEye Spectrophotometer with a 6 inch integrating sphere. The conditions are: 10 degree observer, D65 illuminant and 8 degree viewing angle.

Initial color measurements are taken using the above parameters. The L, a and b values are calculated using the CIE system from the reflectance values. YI is calculated from the L, a and b values. Subsequent measurements are taken at specified intervals. Delta L, a, b and YI values are simply the difference between the initial values and the values at each interval. Delta($\Delta$) E is calculated as follows:

$$[(Delta\ L)^2 + (Delta\ a)^2 + (Delta\ b)^2]^{1/2} = Delta\ E.$$

EXAMPLE 44

Color Fade of White Scented Candle Wax under Fluorescent Lamp Exposure

A variety of different stabilizers are evaluated in white scented candle wax obtained from the Candle-Lite Corporation under fluorescent lamp exposure. The $\Delta$E values represent the change in color after the indicated days of exposure. A low $\Delta$E value indicates less change in color and is highly desired.

| Sample* (wt % add) | $\Delta$E after 5.9 days | $\Delta$E after 11.8 days | $\Delta$E after 35 days |
|---|---|---|---|
| Blank (no add) | 42.90 | 45.50 | 45.14 |
| A (0.15%) + B (0.15%) | 24.48 | 26.36 | 27.80 |
| C (0.15%) + D (0.15%) | 13.34 | 15.26 | 18.16 |
| C (0.15%) + E (0.15%) | 14.82 | 22.44 | 25.86 |
| C (0.15%) + F (0.15%) | 11.43 | 13.61 | 14.64 |

*A is 2-(2-hydroxy-5-tert-octylphenyl)-2H-benzotriazole, TINUVIN ® 329, CIBA.
B is bis(1,2,2,6,6-pentamethylpiperidin-4-yl) sebacate, TINUVIN ® 292, CIBA.
C is octyl 3-(benzotriazol-2-yl)-5-tert-butyl-4-hydroxyhydrocinnamate, TINUVIN ® 384, CIBA.
D is bis(1-octyloxy-2,2,6,6-tetramethylpiperidin-4-yl) sebacate. TINVVIN ® 123, CIBA.
E is 1-phenoxy-2,2,6,6-tetramethylpiperidine, the compound of Example 1.
F is 1-phenoxy-4-benzoyloxy-2,2,6,6-tetramethylpiperidine, the compound of Example 28.

These data show that the instant compound of Example 28 protects white scented candle from discoloring better than do conventional stabilizer systems.

EXAMPLE 45

Color Fade of Gray Scented Candle Wax under Fluorescent Lamp Exposure

A variety of different stabilizers are evaluated in gray scented candle wax obtained from the Candle-Lite Corporation under fluorescent lamp exposure. The $\Delta$E values represent the change in color after the indicated days of exposure. A low $\Delta$E value indicates less change in color and is highly desired.

| Sample* (wt % add) | $\Delta$E after 4.9 days | $\Delta$E after 15.5 days | $\Delta$E after 33.9 days |
|---|---|---|---|
| Blank (no add) | 9.66 | 14.07 | 16.01 |
| A (0.15%) + B (0.15%) | 0.62 | 0.90 | 1.69 |
| C (0.15%) + D (0.15%) | 1.04 | 1.82 | 3.16 |
| C (0.15%) + E (0.15%) | 1.74 | 2.63 | 4.46 |
| C (0.15%) + F (0.15%) | 1.75 | 2.68 | 4.89 |

*A is 2-(2-hydroxy-5-tert-octylphenyl)-2H-benzotriazole, TINUVIN ® 329, CIBA.
B is bis(1,2,2,6,6-pentamethylpiperidin-4-yl) sebacate, TINUVIN ® 292, CIBA.
C is octyl 3-(benzotriazol-2-yl)-5-tert-butyl-4-hydroxyhydrocinnamate, TINUVIN ® 384, CIBA.
D is bis(1-octyloxy-2,2,6,6-tetramethylpiperidin-4-yl) sebacate. TINVVIN ® 123, CIBA.
E is 1-phenoxy-2,2,6,6-tetramethylpiperidine, the compound of Example 1.
F is 1-phenoxy-4-benzoyloxy-2,2,6,6-tetramethylpiperidine, the compound of Example 28.

These data show that the instant compound of Example 1 and 28 protect gray scented candle from discoloring nearly as well as do conventional stabilizer systems.

EXAMPLE 46

Color Fade of Pink Potpouri Scented Candle Wax under Fluorescent Lamp Exposure

A number of stabilizers are evaluated in pink potpouri scented candle wax obtained from the Candle-Lite Corporation under fluorescent lamp exposure. The $\Delta$E values represent the change in color after the indicated days of exposure. A low $\Delta$E value indicates less change in color and is highly desired.

| Sample* (wt % add) | $\Delta$E after 8.9 days | $\Delta$E after 11.8 days | $\Delta$E after 22.3 days |
|---|---|---|---|
| Blank (no add) | 8.10 | 10.22 | 12.12 |
| A (0.15%) + B (0.15%) | 1.25 | 1.01 | 1.17 |
| C (0.15%) + D (0.15%) | 1.84 | 2.73 | 3.20 |
| C (0.15%) + E (0.15%) | 6.52 | 8.64 | 10.62 |
| C (0.15%) + F (0.15%) | 3.32 | 5.09 | 6.97 |

*A is 2-(2-hydroxy-5-tert-octylphenyl)-2H-benzotriazole, TINUVIN ® 329, CIBA.
B is bis(1,2,2,6,6-pentamethylpiperidin-4-yl) sebacate, TINUVIN ® 292, CIBA.
C is octyl 3-(benzotriazol-2-yl)-5-tert-butyl-4-hydroxyhydrocinnamate, TINUVIN ® 384, CIBA.
D is bis(1-octyloxy-2,2,6,6-tetramethylpiperidin-4-yl) sebacate. TINVVIN ® 123, CIBA.
E is 1-phenoxy-2,2,6,6-tetramethylpiperidine, the compound of Example 1.
F is 1-phenoxy-4-benzoyloxy-2,2,6,6-tetramethylpiperidine, the compound of Example 28.

These data show that the instant compounds of Examples 1 and 28 provide the pink potpouri scented candle some protection from discoloring.

EXAMPLE 47

Color Fade of White Scented Candle Wax under UV Lamp Exposure

A variety of different stabilizers are evaluated in white scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 4 days | ΔE after 10.1 days | ΔE after 33 days |
|---|---|---|---|
| Blank (no add) | 27.56 | 32.71 | 34.68 |
| A (0.15%) + B (0.15%) | 18.66 | 23.57 | 25.09 |
| C (0.15%) + D (0.15%) | 5.16 | 6.68 | 10.27 |
| C (0.15%) + E (0.15%) | 10.44 | 16.62 | 23.03 |
| C (0.15%) + F (0.15%) | 5.77 | 9.39 | 13.16 |

*A is 2-(2-hydroxy-5-tert-octylphenyl)-2H-benzotriazole, TINUVIN ® 329, CIBA.
B is bis(1,2,2,6,6-pentamethylpiperidin-4-yl) sebacate, TINUVIN ® 292, CIBA.
C is octyl 3-(benzotriazol-2-yl)-5-tert-butyl-4-hydroxyhydrocinnamate, TINUVIN ® 384, CIBA.
D is bis(1-octyloxy-2,2,6,6-tetramethylpiperidin-4-yl) sebacate. TINVIN ® 123, CIBA.
E is 1-phenoxy-2,2,6,6-tetramethylpiperidine, the compound of Example 1.
F is 1-phenoxy-4-benzoyloxy-2,2,6,6-tetramethylpiperidine, the compound of Example 28.

These data show that the instant compound of Example 28 protects white scented candle from discoloring far better than do some conventional stabilizer systems.

EXAMPLE 48

Color Fade of Gray Scented Candle Wax under UV Lamp Exposure

A variety of different stabilizers are evaluated in gray scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 2.8 days | ΔE after 8.9 days | ΔE after 22.6 days |
|---|---|---|---|
| Blank (no add) | 22.20 | 28.98 | 30.07 |
| A (0.15%) + B (0.15%) | 1.16 | 2.73 | 3.83 |
| C (0.15%) + D (0.15%) | 1.70 | 3.47 | 5.11 |
| C (0.15%) + E (0.15%) | 1.41 | 3.13 | 5.36 |
| C (0.15%) + F (0.15%) | 1.57 | 3.27 | 5.38 |

*A is 2-(2-hydroxy-5-tert-octylphenyl)-2H-benzotriazole, TINUVIN ® 329, CIBA.
B is bis(1,2,2,6,6-pentamethylpiperidin-4-yl) sebacate, TINUVIN ® 292, CIBA.
C is octyl 3-(benzotriazol-2-yl)-5-tert-butyl-4-hydroxyhydrocinnamate, TINUVIN ® 384, CIBA.
D is bis(1-octyloxy-2,2,6,6-tetramethylpiperidin-4-yl) sebacate. TINVIN ® 123, CIBA.
E is 1-phenoxy-2,2,6,6-tetramethylpiperidine, the compound of Example 1.
F is 1-phenoxy-4-benzoyloxy-2,2,6,6-tetramethylpiperidine, the compound of Example 28.

These data show that the instant compounds of Examples 1 and 28 protect gray scented candle from discoloring as well as do some conventional stabilizer systems.

EXAMPLE 49

Color Fade of Pink Potpouri Scented Candle Wax under UV Lamp Exposure

A number of stabilizer compounds are evaluated in pink potpouri scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 7.6 days | ΔE after 18.4 days | ΔE after 36.7 days |
|---|---|---|---|
| Blank (no add) | 16.16 | 17.47 | 20.27 |
| A (0.15%) + B (0.15%) | 3.18 | 3.60 | 4.35 |
| C (0.15%) + D (0.15%) | 5.12 | 2.84 | 3.44 |
| C (0.15%) + E (0.15%) | 6.35 | 7.76 | 11.07 |
| C (0.15%) + F (0.15%) | 5.83 | 7.05 | 9.26 |

*A is 2-(2-hydroxy-5-tert-octylphenyl)-2H-benzotriazole, TINUVIN ® 329, CIBA.
B is bis(1,2,2,6,6-pentamethylpiperidin-4-yl) sebacate, TINUVIN ® 292, CIBA.
C is octyl 3-(benzotriazol-2-yl)-5-tert-butyl-4-hydroxyhydrocinnamate, TINUVIN ® 384, CIBA.
D is bis(1-octyloxy-2,2,6,6-tetramethylpiperidin-4-yl) sebacate. TINVIN ® 123, CIBA.
E is 1-phenoxy-2,2,6,6-tetramethylpiperidine, the compound of Example 1.
F is 1-phenoxy-4-benzoyloxy-2,2,6,6-tetramethylpiperidine, the compound of Example 28.

These data show that the instant compounds of Examples 1 and 28 provide the pink potpouri scented candle with some protection from discoloring.

What is claimed is:

1. A process for preparing a sterically hindered N-aryloxyamine of formula I, II, III, IV, V or VI

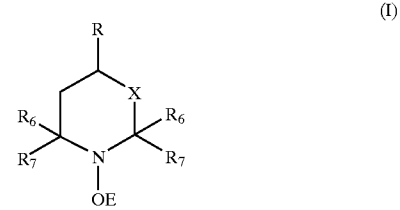

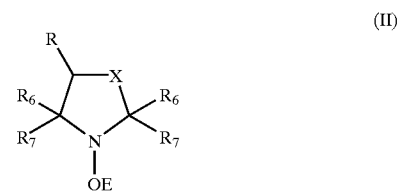

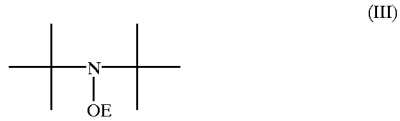

-continued (IV)
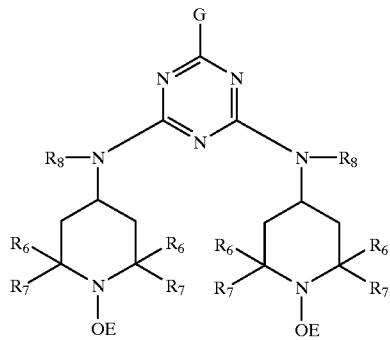

(V)
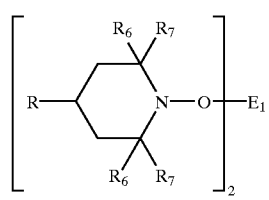

(VI)
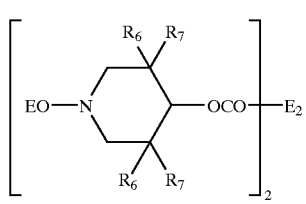

which comprises
  reacting a sterically hindered nitroxyl compound of formula VII, VIII, IX, X or XI (VII)
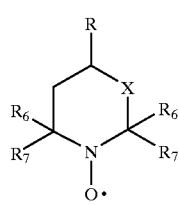

(VIII)
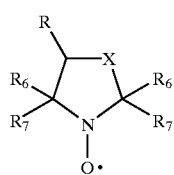

(IX)
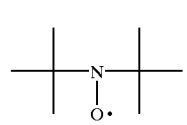

(X)
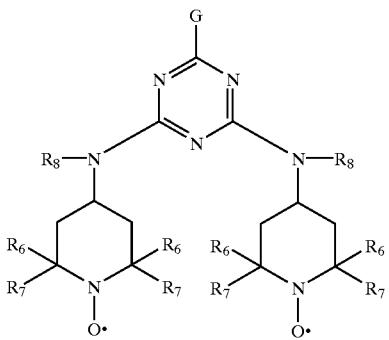

(XI)
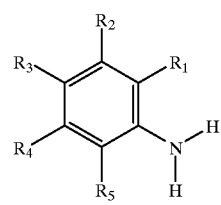

with a diazonium salt of an aromatic amine of formula XII, XIII or XIV (XII)
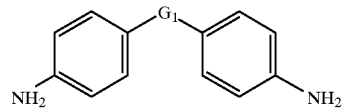

(XIII)

or (XIV)

in the presence of a transition-metal catalyst
wherein
  X is —$CH_2$—, —O—, —S— or —$NR_8$— where $R_8$ is hydrogen or alkyl of 1 to 12 carbon atoms,
  $R_6$ and $R_7$ are independently alkyl of 1 to 8 carbon atoms, or $R_6$ and $R_7$ together are tetramethylene or pentamethylene, E is 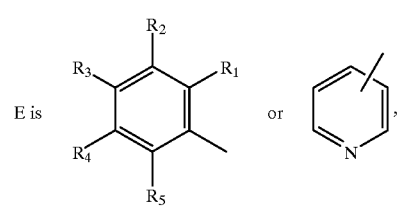

$E_1$ is

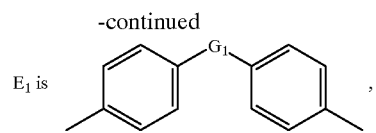

$E_2$ is alkylene of 2 to 12 carbon atoms,
$G$ is chloro or —N(2-ethylhexyl)$_2$,
$G_1$ is —CH$_2$—, —CO— or —O—,
R is hydrogen, alkyl of 1 to 18 carbon atoms, aralkyl of 7 to 15 carbon atoms, aryl of 6 to 10 carbon atoms, hydroxyl, carboxyl, amino, alkylamino of 1 to 18 carbon atoms, dialkylamino of 2 to 36 carbon atoms, oxo, alkylthio of 1 to 18 carbon atoms, alkoxy of 1 to 18 carbon atoms, aryloxy of 7 to 15 carbon atoms, benzoyloxy, alkylcarbonyloxy of 2 to 18 carbon atoms or alkylcarbonylamino of 2 to 18 carbon atoms, and $R_1$ to $R_5$ are independently hydrogen, halogen, nitro, cyano, alkyl of 1 to 18 carbon atoms, aralkyl of 7 to 15 carbon atoms, aryl of 6 to 10 carbon atoms, hydroxyl, carboxyl, alkylthio of 1 to 18 carbon atoms, alkoxy of 1 to 18 carbon atoms, aryloxy of 7 to 15 carbon atoms, alkylcarbonyloxy of 1 to 18 carbon atoms, alkylsulfonyl of 1 to 18 carbon atoms, arylsulfonyl of 6 to 15 carbon atoms, sulfo or —P(O)(OH)$_2$ or —P(O)(OR$_6$)$_2$, or any two vicinal substituents connected together form a mono or polycyclic ring; or any two vicinal carboxyl groups can be joined to form an imide; or $R_3$ is

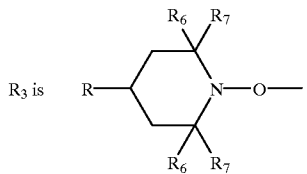

where R, $R_6$ and $R_7$ are as defined above;
or $R_3$ is trifluoromethyl.

2. A process according to claim 1 wherein X is methylene.

3. A process according to claim 1 wherein R is hydrogen, hydroxyl, oxo or acetamido.

4. A process according to claim 1 wherein $R_1$ to $R_5$ are each hydrogen; or $R_1$ is nitro, $R_3$ is chloro or trifluoromethyl, and $R_2$, $R_4$ and $R_5$ are hydrogen; or $R_1$ and $R_3$ are bromo, and $R_2$, $R_4$ and $R_5$ are hydrogen.

5. A process according to claim 1 wherein $R_6$ and $R_7$ are each methyl.

6. A process according to claim 1 wherein $R_1$ and $R_3$ are each bromo or chloro.

7. A process according to claim 1 wherein the N-aryloxyamine is (a) 1-phenoxy-2,2,6,6-tetramethylpiperidine;
(b) 1-phenoxy-2,2,6,6-tetramethyl-4-hydroxypiperidine;
(c) 1-(2-nitro-4-trifluoromethylphenoxy)-2,2,6,6-tetramethylpiperidine;
(d) 1-(2-nitro-4-chlorophenoxy)-2,2,6,6-tetramethylpiperidine;
(e) 1-(2,4-dibromophenoxy)-2,2,6,6-tetramethylpiperidine;
(f) 1-(2,4-dibromophenoxy)-4-hydroxy-2,2,6,6-tetramethylpiperidine;
(g) 1-(2,4-dibromophenoxy)-4-acetamido-2,2,6,6-tetramethylpiperidine;
(h) 1-(2,4-dibromophenoxy)-4-oxo-2,2,6,6-tetramethylpiperidine;
(i) 1-(2-naphthyloxy)-2,2,6,6-tetramethylpiperidine;
(j) 1-(4-benzoylphenoxy)-2,2,6,6-tetramethylpiperidine;
(k) 1-phenoxy-4-benzoyloxy-2,2,6,6-tetramethylpiperidine;
(l) N-phenoxy-di-tert-butylamine;
(m) 2,4-bis[N-butyl-N-(1-phenoxy-2,2,6,6-tetramethylpiperidin-4-yl)amino]-6-chloro-s-triazine;
(n) 2,4-bis{N-butyl-N-[1-(2,4-dibromophenoxy)-2,2,6,6-tetramethylpiperidin-4-yl]amino}-6-[N,N-bis(2-ethylhexyl)amino]-s-triazine;
(o) 2,4-bis[N-butyl-N-(1-phenoxy-2,2,6,6-tetramethylpiperidin-4-yl)amino]-6-[N,N-bis(2-ethylhexyl)amino]-s-triazine;
(p) 1-(3,5-di-tert-butylphenoxy)-2,2,6,6-tetramethylpiperidine;
(q) 1-(pyridin-3-yloxy)-2,2,6,6-tetramethylpiperidine;
(r) 1-(2-nitro-4-chlorophenoxy)-2,2,6,6-tetramethyl-4-hydroxypiperidine;
(s) 4,4'-bis(2,2,6,6-tetramethylpiperidin-1-yloxy)benzophenone;
(t) di(1-phenoxy-2,2,6,6-tetramethyl-piperidin-4-yl)sebacate;
(u) 1-phenoxy-3-carboxyl-2,2,5,5-tetramethylpyrrolidine;
(v) 4,4'-bis[(4-hydroxy-2,2,6,6-tetramethylpiperidin-1-yl)oxy]diphenylmethane; or
(w) 1-(phthalimid-4-yloxy)-4-hydroxy-2,2,6,6-tetramethylpiperidine.

8. A process according to claim 1 wherein the diazonium salt of the aromatic amine of formula XII is prepared by reaction with an alkyl nitrite.

9. A process according to claim 8 wherein the alkyl nitrite is tert-butyl nitrite.

10. A process according to claim 1 wherein reaction is carried out in acetonitrile as a solvent at a temperature of 0 to 100° C.

11. A process according to claim 10 wherein the temperature is between 20 and 70° C.

12. A process according to claim 1 wherein the reaction is carried out with pyridine present as a reaction component or as a solvent.

13. A process according to claim 1 wherein the transition metal is a metal of Group 4, 5, 6, 7, 8, 9 or 10 of the periodic table.

14. A process according to claim 13 wherein the transition metal is copper(I), copper(II), cobalt(II), manganese(II), titanium(III), iron(II), iron(III), nickel(II), gold(I) or chromium(III).

15. A process according to claim 1 wherein the process is carried out in the presence of 0.1 mole % to stoichiometric quantities of the transition metal catalyst.

16. A process according to claim 1 wherein the the transition metal catalyst is copper(I) or copper(II).

17. A process according to claim 16 wherein the transition metal catalyst is copper(II) fluoride.

18. A process according to claim 13 wherein the transition metal catalyst is gold(I) chloride.

19. A process according to claim 13 wherein the transition metal catalyst is (S,S)-(+)-N,N-bis(3,5-di-tert-butylsalicylidene)-1,2-cyclohexanediaminocobalt(II), N,N-bis(salicylidene)ethylenediaminocobalt(II) or (R,R)-(−)-N, N-bis(3,5-di-tert-butylsalicylidene)-1,2-cyclohexanediaminocobalt(II).

20. A compound which is
(i) 1-(2-nitro-4-trifluoromethylphenoxy)-2,2,6,6-tetramethylpiperidine;
(ii) 1-(2-nitro-4-chlorophenoxy)-2,2,6,6-tetramethylpiperidine;
(iii) 1-(2,4-dibromophenoxy)-2,2,6,6-tetramethylpiperidine;
(iv) 1-(2,4-dibromophenoxy)-4-hydroxy-2,2,6,6-tetramethylpiperidine;
(v) 1-(2,4-dibromophenoxy)-4-acetamido-2,2,6,6-tetramethylpiperidine;
(vi) 1-(2,4-dibromophenoxy)-4-oxo-2,2,6,6-tetramethylpiperidine;
(vii) 1-(2-naphthyloxy)-2,2,6,6-tetramethylpiperidine;
(viii) 1-(4-benzoylphenoxy)-2,2,6,6-tetramethylpiperidine;
(xi) 2,4-bis[N-butyl-N-(1-phenoxy-2,2,6,6-tetramethylpiperidin-4-yl)amino]-6-chloro-s-triazine;
(xii) 2,4-bis{N-butyl-N-[1-(2,4-dibromophenoxy)-2,2,6,6-tetramethylpiperidin-4-yl]amino}-6-[N,N-bis(2-ethylhexyl)amino]-s-triazine;
(xiii) 2,4-bis[N-butyl-N-(1-phenoxy-2,2,6,6-tetramethylpiperidin-4-yl)amino]-6-[N,N-bis(2-ethylhexyl)amino]-s-triazine;
(xiv) 1-(3,5-di-tert-butylphenoxy)-2,2,6,6-tetramethylpiperidine;
(xv) 1-(pyridin-3-yloxy)-2,2,6,6-tetramethylpiperidine;
(xvi) 1-(2-nitro-4-chlorophenoxy)-2,2,6,6-tetramethyl-4-hydroxypiperidine;
(xvii) 4,4'-bis(2,2,6,6-tetramethylpiperidin-1-yloxy)benzophenone;
(xviii) di(1-phenoxy-2,2,6,6-tetramethyl-piperidin-4-yl) sebacate;
(xix) 1-phenoxy-3-carboxyl-2,2,5,5-tetramethylpyrrolidine;
(xx) 4,4'-bis[(4-hydroxy-2,2,6,6-tetramethylpiperidin-1-yl)oxy]diphenylmethane, or
(xxi) 1-(phthalimid-4-yloxy)-4-hydroxy-2,2,6,6-tetramethylpiperidine.

21. A process according to claim 1 wherein the diazonium salt of the aromatic amine of formula XII is prepared by reaction of the amine with an alkali metal nitrite and an aqueous mineral acid.

22. A stabilized composition which comprises
(a) an organic material subject to degradation by heat, light or oxygen, and
(b) an effective stabilizing amount of a compound of formula I, II, III, IV, V or VI as described in claim 1, with the proviso that when the organic material is polypropylene, the compound of formula I is excluded when R is alkylcarbonyloxy, X is —CH$_2$— and R$_1$–R$_5$ are each hydrogen.

23. A composition which comprises
(a) candle wax which is white and scented, white and unscented, dyed and scented, dyed and unscented, dipped and scented or dipped and unscented, and
(b) an effective stabilizing amount of a compound of formula I, II, III, IV, V or VI

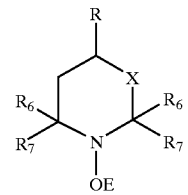
(I)

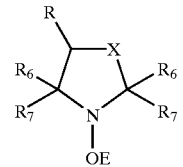
(II)

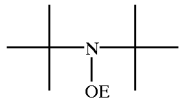
(III)

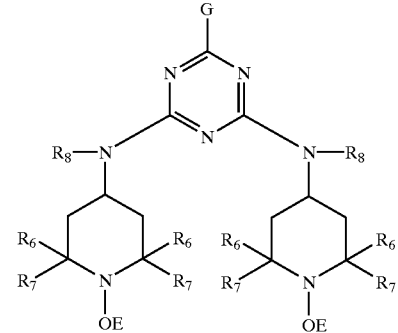
(IV)

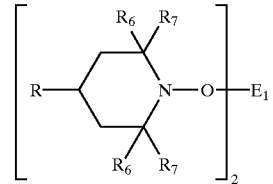
(V)

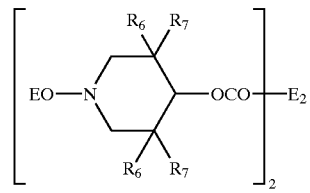
(VI)

wherein

X is —CH$_2$—, —O—, —S— or —NR$_8$— where R$_8$ is hydrogen or alkyl of 1 to 12 carbon atoms, R$_6$ and R$_7$ are independently alkyl of 1 to 8 carbon atoms, or R$_6$ and R$_7$ together are tetramethylene or pentamethylene, E is 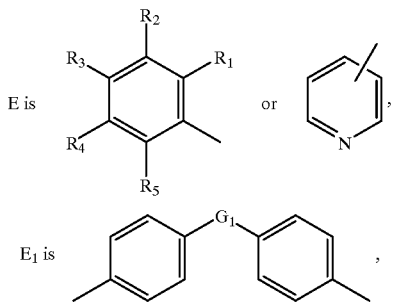 or E₁ is 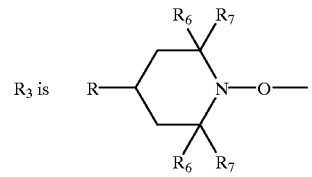, $E_2$ is alkylene of 2 to 12 carbon atoms,
G is chloro or —N(2-ethylhexyl)₂,
$G_1$ is —CH₂—, —CO— or —O—,
R is hydrogen, alkyl of 1 to 18 carbon atoms, aralkyl of 7 to 15 carbon atoms, aryl of 6 to 10 carbon atoms, hydroxyl, carboxyl, amino, alkylamino of 1 to 18 carbon atoms, dialkylamino of 2 to 36 carbon atoms, oxo, alkylthio of 1 to 18 carbon atoms, alkoxy of 1 to 18 carbon atoms, aryloxy of 7 to 15 carbon atoms, benzoyloxy, alkylcarbonyloxy of 2 to 18 carbon atoms or alkylcarbonylamino of 2 to 18 carbon atoms, and
$R_1$ to $R_5$ are independently hydrogen, halogen, nitro, cyano, alkyl of 1 to 18 carbon atoms, aralkyl of 7 to 15 carbon atoms, aryl of 6 to 10 carbon atoms, hydroxyl, carboxyl, alkylthio of 1 to 18 carbon atoms, alkoxy of 1 to 18 carbon atoms, aryloxy of 7 to 15 carbon atoms, alkylcarbonyloxy of 1 to 18 carbon atoms, alkylsulfonyl of 1 to 18 carbon atoms, arylsulfonyl of 6 to 15 carbon atoms, sulfa or —P(O)(OH)₂ or —P(O)(OR₆)₂, or any two vicinal substituents connected together form a mono or polycyclic ring, or any two vicinal carboxyl groups can be joined to form an imide; or $R_3$ is where R, $R_6$ and $R_7$ are as defined above;

or $R_3$ is trifluoromethyl.

24. A composition according to claim 23 which additionally contains an effective stabilizing amount of a UV absorber.

* * * * *